United States Patent [19]

Perten

[11] Patent Number: 5,308,981
[45] Date of Patent: May 3, 1994

[54] METHOD AND DEVICE FOR INFRARED ANALYSIS, ESPECIALLY WITH REGARD TO FOOD

[76] Inventor: Peter Perten, Unt. Grundlistrasse 12, CH-6055 Alpnach Dorf, Switzerland

[21] Appl. No.: 872,693

[22] Filed: Apr. 23, 1992

[30] Foreign Application Priority Data

Apr. 23, 1991 [SE] Sweden .................... 9101220-3

[51] Int. Cl.$^5$ .................................... G01N 21/35
[52] U.S. Cl. ............................ 250/339.01; 250/341; 250/358.1; 356/418
[58] Field of Search ............... 250/339, 343, 341, 351, 250/358.1; 356/418

[56] References Cited

U.S. PATENT DOCUMENTS

| | | | |
|---|---|---|---|
| 3,776,642 | 12/1973 | Anson et al. | 356/188 |
| 4,260,262 | 4/1981 | Webster | 356/418 |
| 4,404,642 | 9/1983 | Rosenthal | 250/339 |
| 4,422,760 | 12/1983 | Webster | 356/244 |
| 4,466,076 | 8/1984 | Rosenthal | 250/339 |
| 4,479,055 | 10/1984 | Perten | 250/343 |
| 4,540,286 | 9/1985 | Satake et al. | 356/445 |
| 4,734,584 | 3/1988 | Rosenthal | 250/343 |
| 4,742,228 | 5/1988 | Bischoff | 250/341 |
| 4,752,689 | 6/1988 | Satake | 250/341 |
| 4,866,644 | 9/1989 | Shenk et al. | 356/418 |
| 4,963,743 | 10/1990 | Satake et al. | 250/341 |

FOREIGN PATENT DOCUMENTS 0240185 10/1987 European Pat. Off. .

OTHER PUBLICATIONS

Rosenthal, "Characteristics of Non-Destructive Near-IR Instruments For Grain And Food Products", 1986 pp. 1-23.

"Near-Infrared Reflectance Analysis", *Analytical Chemistry*, vol. 55, No. 12, Oct. 1983, By D. Wetzel, pp. 1165A-1176A.

Primary Examiner—Paul M. Dzierzynski
Assistant Examiner—Drew A. Dunn
Attorney, Agent, or Firm—Young & Thompson

[57] ABSTRACT

In analysis of a sample of unground grain, infrared light is directed towards the sample and is detected after reflection on the sample. For analysis of wheat, light wavelengths within the interval 1050-1400 nm are used with a light detector of PbS-type. A suitable infrared analyzer has a rotatable filter device (5) with a plurality of filters (4) within the stated wavelength interval and is disposed to be able to carry out in a short time period a large number of measurements.

10 Claims, 1 Drawing Sheet

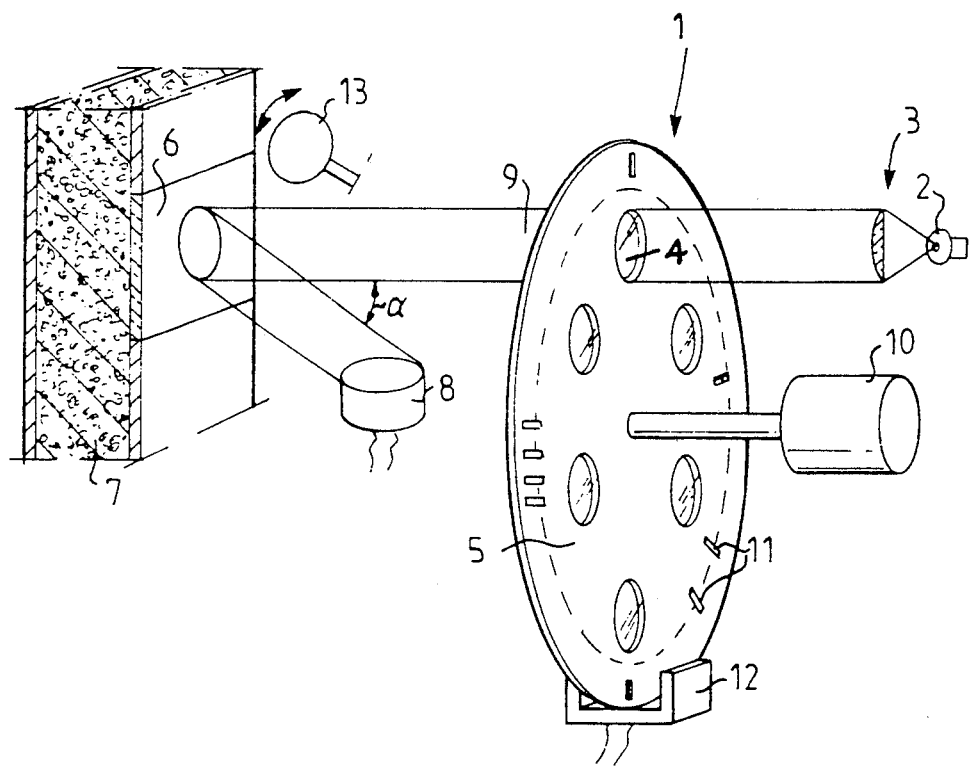

METHOD AND DEVICE FOR INFRARED ANALYSIS, ESPECIALLY WITH REGARD TO FOOD

FIELD OF THE INVENTION

The present invention relates to a method of analysis of a sample, especially a food sample, whereby certain wave lengths of infrared light are directed towards the sample and after passage thereof are detected by means of a photocell device to determine the relative amount of certain substances in the sample. The invention also relates to a device for carrying out said method.

BACKGROUND OF THE INVENTION

It is known to determine the chemical composition of a sample with the aid of infrared analysis, whereby infrared light is either reflected against a sample or is allowed to penetrate through a sample. By measuring the amount of energy absorbed by the sample at certain wave lengths, it is possible to determine the chemical composition of the product. This is utilized in a variety of different contexts, inter alia in the food industry, for product analysis.

In the flour milling industry, it has been the practice for many years to check the flour quality with the aid of infrared analysis as described above, and in this case reflection analysis has been used, i.e. reflected light from the sample has been measured.

It has, however, been a long felt need to be able to perform effective and rapid analysis of unmilled grain, for the purpose of better quality sorting of different shipments of grain. Tests have shown that equipment which has, up to now, usually been used for reflection analysis of flour, and in which light detectors of lead sulphide type have been used, has not been usable for whole grain analysis, since the signals obtained have proved to be too small in order to be of any practical use. It has instead been suggested to perform whole grain analysis by transmission measurement of wave lengths of less than 1100 nm and using light detectors of silicon type, see for example U.S. Pat. No. 4,286,237. One disadvantage is, however, that analysis can only be performed on relatively thin layers of grain, where the thickness does not exceed 25 or 30 mm. It is also proved difficult to perform analysis on samples which are in motion relative to the analysis equipment, i.e. to measure a continuous flow of grain. Another disadvantage is that any variations between a number of light sources used will affect the measurements negatively.

SUMMARY OF THE INVENTION

The purpose of the invention is to make possible analysis of unground products, such as grain, in a more simple, better and more rapid manner than previously.

This purpose is achieved in a method according to the invention by virtue of the fact that detection is carried out on reflected light from a sample of unground grain, that light wave lengths within the interval 1050–1400 nm are used, and that an analysis value is created as a mean value of measurement results obtained in measurements of at least 30 different sample configurations.

According to the invention, it is of advantage that the measurements be carried out within 10 seconds. Analysis can thus be carried out while the sample is in movement relative to the analysis equipment. It is especially suitable for light detection to use a detector of lead sulphide type.

An infrared analyzer of the type to which the invention relates and which is designed for determining the relative amounts of certain substances in a sample, especially a food sample, is constructed such that between a light source and a sample container, there is arranged a filter device from which only infrared light of one specific wave length at a time can reach the sample, there being a photocell device for detecting light from each sample. This infrared analyzer is characterized according to the invention in that the photocell device in a known manner is disposed between the filter device and the sample to detect reflected light from the sample, that the filter device includes a continuously rotatable disc which is provided with a number of different filters to let light through in the interval 1050–1400 nm, that in the photocell device there is at least one detector of lead sulphide type, and that the analyzer is disposed to register measured values during rotation of the filter disc.

It has proved possible through the invention by using somewhat different wavelengths than those which could be used previously for reflection analysis of flour, to be able to carry out analysis of unground grain. Possibilities have thus been opened for rapid and simple quality sorting of grains in a manner which was not possible previously immediately upon taking delivery of the grain.

BRIEF DESCRIPTION OF THE DRAWING

The invention will be explained below in more detail with the aid of an example, shown schematically in the accompanying drawing, of an infrared analyzer according to the invention.

DETAILED DESCRIPTION OF THE INVENTION

An infrared analyzer 1 according to the invention and shown in the drawing has a light source 2, which, via an optical system 3, emits light towards a filter 4 in a filter disc or filter device 5 provided with a number of monochromatic filters. This filter disc is rotatable so that one filter at a time can be subjected to light. By virtue of the fact that the filters are adapted to permit passage of different specific wavelengths, depending on the filter used, be directed to a window 6 of a sample container, behind which where is a sample 7 of unground grain which is possibly in movement, suitably vertically.

Reflected light from the sample 7 photocell device or light detector 8, which is located relatively near to the window 6 but to one side of the beam 9 striking the window 6 perpendicularly. This light detector 8 is of PbS-type and can be placed with advantage so that it is struck by rays which are reflected at an angle $\alpha$ from the incident beam 9. The angle $\alpha$ can with advantage be about 45°. Additional light detectors 8 distributed about the light beam 9 are also possible.

The filter disc 5 is continuously rotatable by means of a motor 10 and has the filters 4 placed with such circumferential spacing that only one filter at a time can be subjected to light. The spacing between the filters should be at least one filter diameter. Radially outside the filters 4, the filter disc 5 is provided with a number of uniformly spaced apertures 11. During the rotation of the filter disc, these apertures 11, which suitably have the shape of radially extending slots, pass a positional sensor 12 securely mounted in the analyzer 1, to thereby make it possible to sense the current rotational position of the filter disc. The positional sensor 12 consists of a detector fork of the type where a light source and a light detector are on either side of the filter disc 5 and can thus indicate each aperture 11 which passes. By registering the signal from the light detector 8 at certain rotational positions of the filter disc 5 (determined with the aid of the positional sensor 12), it is possible, with the sufficient number of apertures 11, to, under one rotation of the filter disc, to register at least one signal reading from the light detector 8 for each filter 4. Instead of being reflected against the sample 7, light can be reflected in a well-known manner at selected occasions against a reference surface 13, which can be swung into the beam of light 9 when a suitable filter is illuminated.

When measuring reflected light from a sample consisting of whole grains of wheat, poor reproducability was obtained between the individual tests, due to how the grains of wheat happened to be oriented in each individual test. By making measurements of many tests, however, i.e. with many different configurations of wheat grains, and by computing mean values of these many measurements, it has proved possible to achieve a good accuracy of analysis, with a standard deviation within 0.1-0.2%.

In order to reduce purely electronic measuring errors, it has proved suitable, for each sample configuration, to generate the measurement results for the different filters as the mean value of a number of individual measurements, i.e. measurements for several rotations of the filter disc 5, e.g. two, four, six or more rotations per configuration. By allowing the filter disc 5 to rotate rapidly, i.e. 25 rps, it is possible to make at least 25 measurements per second for each filter. If the number of apertures 11 is great in relation to the number of filters 4, there will be a plurality of possible measuring points for each filter, representing different measurement locations for each filter. It will thus be possible to calculate a mean value for each specific measuring location on each filter, thus making it possible to reduce the effect of variations in the local transmission of the different filters.

The great rapidity of measurement described above makes it possible to make sufficiently many measurements even for samples in motion relative to the window 6, presupposing of course that the movement is not all too rapid.

It has proved possible according to the invention with a light detector 8 of PbS-type to carry out analysis of unground grain by using absorption bands within the wavelength interval 1050-1400 nm. An especially advantageous wavelength combination has proved to be 1128, 1138, 1154, 1188, 1200 and 1212 nm. This combination has made it possible to analyze the content of protein, water, starch and fat in whole grains of wheat. In addition to the wavelenghts mentioned, it is also possible with advantage to use the wavelengths 1218, 1254 and 1320 nm to refine the analysis.

As was mentioned above, a number of measurements are made for each filter against a reference and against different samples. After converting the signal amplitudes measured from analog to digital form in an A/D converter, the mean value $R_m$ is computed from the reference signal amplitudes and the mean value $P_m$ of the sample signal amplitudes. Thereafter, there is computed the logarithm for the quotient $R_m/P_m$ for the filter in question, i.e. for the quotient $(R_m/P_m)_i$ where the index i indicates which filter is intended. This is done in a processor coupled to the light detector 8 and the position indicator 12.

It has been shown that the deviation between different samples will be relatively great when the particle size in the sample exceeds about 1 mm, and increases with increased particle size, due inter alia to the fact that there will then be relatively much air between the particles (the cereal grains). In order to improve the reproducability between different subsamples with large particles, a correction is suggested of the measured value in accordance with the following:

$$\log'(R_m/P_m)_i = \frac{\log(R_m/P_m)_i - \log(R/P)_{Ref.\ 1}}{\log(R/P)_{Ref.\ 2} - \log(R/P)_{Ref.\ 1}}$$

Here Ref 1 represents a first reference filter with a low wavelength, and Ref 2 represents a second reference filter with a high wavelength. These two wavelengths are selected so that they do not provide any absorption for those components which one is measuring for. The first, low reference wavelength can, for example, at an absorption interval of 1100-1250 nm, be 1077 nm while the other, higher reference wavelength can be 1280 nm. Normally, the value $(R/P)_{Ref\ 1}$ is significantly less than the corresponding value $(R/P)_{Ref\ 2}$, which will mean that the formula, at low values of $(R_m/P_m)_i$, will give a value close to zero, but for high values of $(R_m/P_m)_i$, will have a value close to 1. This correction means that for large particles, there will be a uniform scale where the value curve goes through the origin and the value one. Finely ground samples do not have the same need for correction.

The percentage of protein in grain can be determined by a formula of the type $$k_0 + K_1\log(R_m/P_m)_1 + k_2\log(R_m/P_m)_2 + \ldots + k_i\log(R_mP_m)_i$$

where i is the number of filters and $k_0' \ldots k_i$ are constants, which are determined according to the least squares method. For large particles, the terms involved are corrected according to the above, i.e. the log values are replaced with log' values.

The infrared analyzer 1 according to the invention is of course enclosed in a manner not shown in a case so that outside light cannot affect the measurements. The principle of a reflection analyzer is described in detail in, inter alia, U.S. Pat. No. 4,479,055 and is well known among persons skilled in the art.

The number of filters 4 in the filter disc 5, as well as the wavelength ranges for the filters, can of course be varied as needed, depending on the type of grain or other unground product which one desires to analyze.

I claim:

1. A method of analyzing a sample (7) of grain comprising the steps of;
   a) directing infrared light of certain wavelengths toward the sample,
   b) detecting the infrared light by means of a photocell device (8) after interaction of the infrared light with the sample,
   c) using the detected infrared light to determine the relative amount of certain substances in the sample, the improvement comprising;
   d) directing infrared light within the interval of 1050-1400 nm toward a sample of unground grain,
   e) detecting the infrared light which is reflected from the unground grain, f) analyzing the sample is done by generating an analysis value as a mean value measurement wherein the results are obtained in measurements of at least 30 different sample configurations.

2. Method according to claim 1, wherein the totality of the measurements is carried out within 10 seconds.

3. Method according to claim 1, wherein analyzing the sample is carried out while the sample is in movement relative to the photocell device.

4. Method according to claim 1, wherein the light detecting is done by a detector of lead sulphide type.

5. Method according to claim 1, wherein predetermined wavelengths of 1128, 1138, 1154, 1188, 1200, and 1212 nm are used in analyzing wheat.

6. Method according to claim 5, wherein wavelengths 1218, 1254, and 1320 nm are also used in analyzing wheat.

7. Method according to claim 1, wherein the grain is caused to move downwardly along a vertical path during analyzing the sample.

8. In an infrared analyzer for determining relative amounts of certain substances in a sample of unground grain, wherein between a light source (2) and a sample container having a window (6), there is arranged a filter device (5) from which only infrared light of one specific wavelength at a time can reach the sample (7), and there being a photocell device (8) for detecting light from the sample; the improvement in which the photocell device (8) is disposed between the filter device (5) and the sample (7) to detect reflected light from the sample, the filter device (5) includes a continuously rotatable disc, which is provided with a number of different filters (4) to let light through in the interval 1050–1400 nm, in the photocell device (8) there is at least one detector of lead sulphide type, and the analysis is disposed to register measured values during rotation of the filter disc (5), and means defined a vertical path for the grain along which path the grain moves downwardly during analysis, said means having a transparent window (6) through which the light passes from the filter device (5) to the sample and from the sample to the photocell device (8).

9. Infrared analyzer according to claim 8, wherein the filter device (5) is provided with separate filters (4) for at least 1128, 1138, 1154, 1188, 1200, and 1212 nm.

10. Infrared analyzer according to claim 9, wherein in the filter device (5) there is also included filters (4) for 1218, 1254, and 1320 nm.

* * * * *